United States Patent [19]

Sterrett et al.

[11] Patent Number: 5,013,238

[45] Date of Patent: May 7, 1991

[54] ASEPTIC ORTHODONTIC DISPENSING APPLIANCES

[75] Inventors: Terry L. Sterrett, Long Beach; Gerald W. Schmidt, Ventura, both of Calif.

[73] Assignee: Ormco Corporation, Glendora, Calif.

[21] Appl. No.: 301,122

[22] Filed: Jan. 25, 1989

[51] Int. Cl.⁵ .............................................. A61C 3/00
[52] U.S. Cl. ......................................... 433/2; 433/18; 221/310; 206/63.5; 206/805
[58] Field of Search ................. 433/2, 3, 4, 13, 15, 433/18, 22; 221/310, 312 C; 224/217, 218, 219; 206/348, 445, 303, 63.3, 63.5, 805

[56] References Cited

U.S. PATENT DOCUMENTS

| | | | |
|---|---|---|---|
| 899,664 | 9/1908 | Goodrich | 206/348 |
| 1,401,736 | 12/1921 | Rothschild | 206/348 |
| 2,289,642 | 7/1942 | Flood | 242/55.2 |
| 3,193,094 | 7/1965 | Schulstad | 206/63.5 |
| 3,438,486 | 8/1966 | Pinkas | 206/56 |
| 3,458,031 | 7/1969 | Hoffman | 433/3 |
| 3,530,583 | 4/1969 | Klein et al. | 433/18 |
| 3,803,715 | 4/1974 | Wallshein | 32/14 A |
| 3,903,601 | 9/1975 | Anderson | 32/14 D |
| 3,913,228 | 10/1975 | Wallshein | 32/14 A |
| 4,026,021 | 5/1977 | Kesling | 433/2 |
| 4,034,853 | 7/1977 | Smith | 206/278 |
| 4,038,753 | 8/1977 | Klein | 32/14 E |
| 4,054,997 | 10/1977 | Wallshein | 32/14 A |
| 4,106,374 | 8/1978 | Dragan | 81/302 |
| 4,203,515 | 5/1980 | Kahn | 206/63.5 |
| 4,217,686 | 8/1980 | Dragan | 29/413 |
| 4,330,271 | 5/1982 | Anderson | 433/3 |
| 4,412,820 | 11/1983 | Brummond | 433/18 |
| 4,570,868 | 2/1986 | Wiggs et al. | 242/55.53 |
| 4,576,311 | 3/1986 | Horton et al. | 221/73 |
| 4,626,313 | 12/1986 | Karp | 156/362 |
| 4,668,186 | 5/1987 | Bally et al. | 433/3 |
| 4,946,385 | 8/1990 | Eckert et al. | 433/18 |

Primary Examiner—Cary E. Stone
Attorney, Agent, or Firm—Marjama & Pincelli

[57] ABSTRACT

Dispensing device for dispensing orthodontic O-rings wherein the O-rings are individually dispensed and are easily accessible.

9 Claims, 8 Drawing Sheets

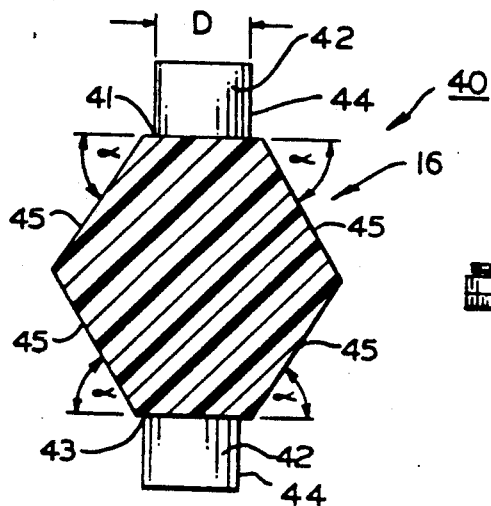
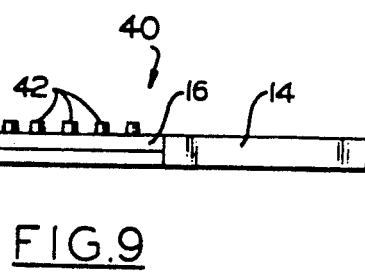
FIG.10   FIG.9
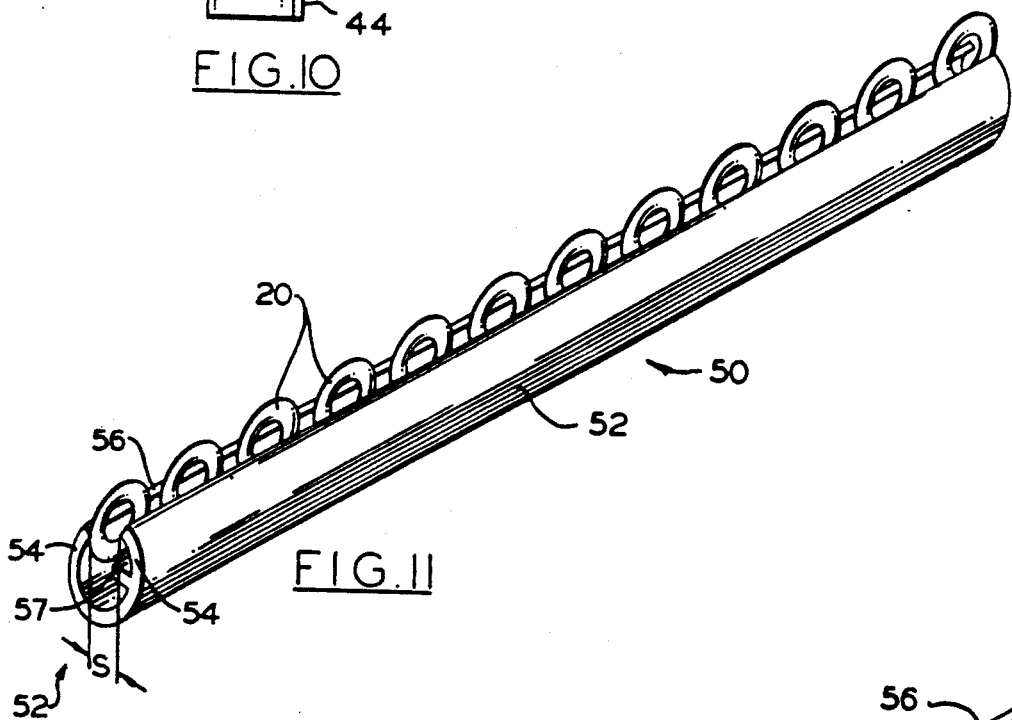
FIG.11
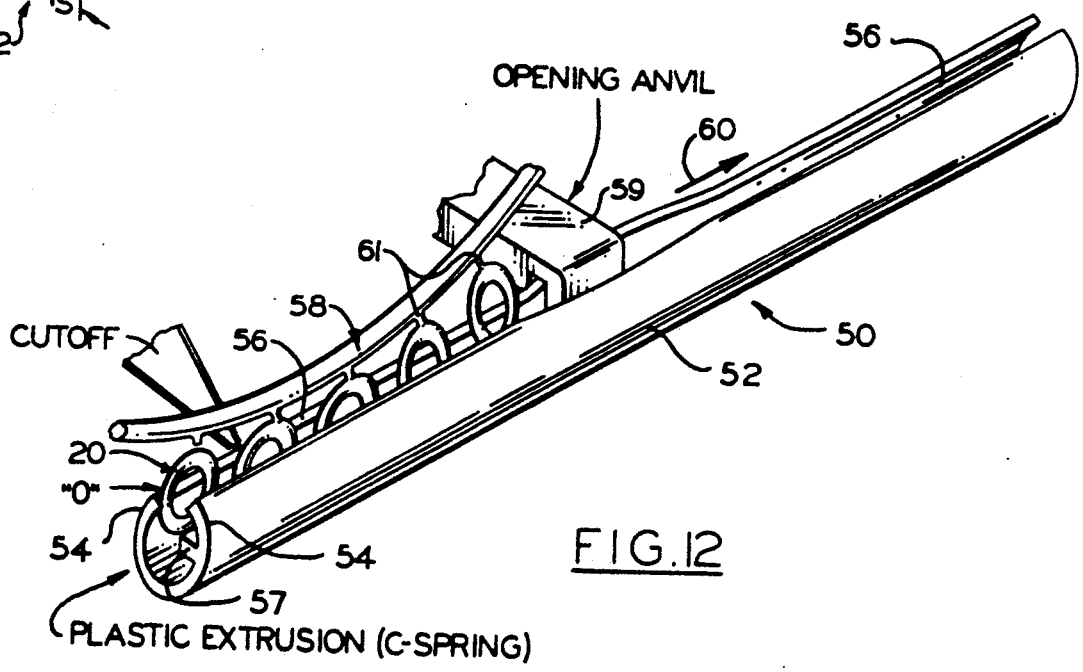
FIG.12

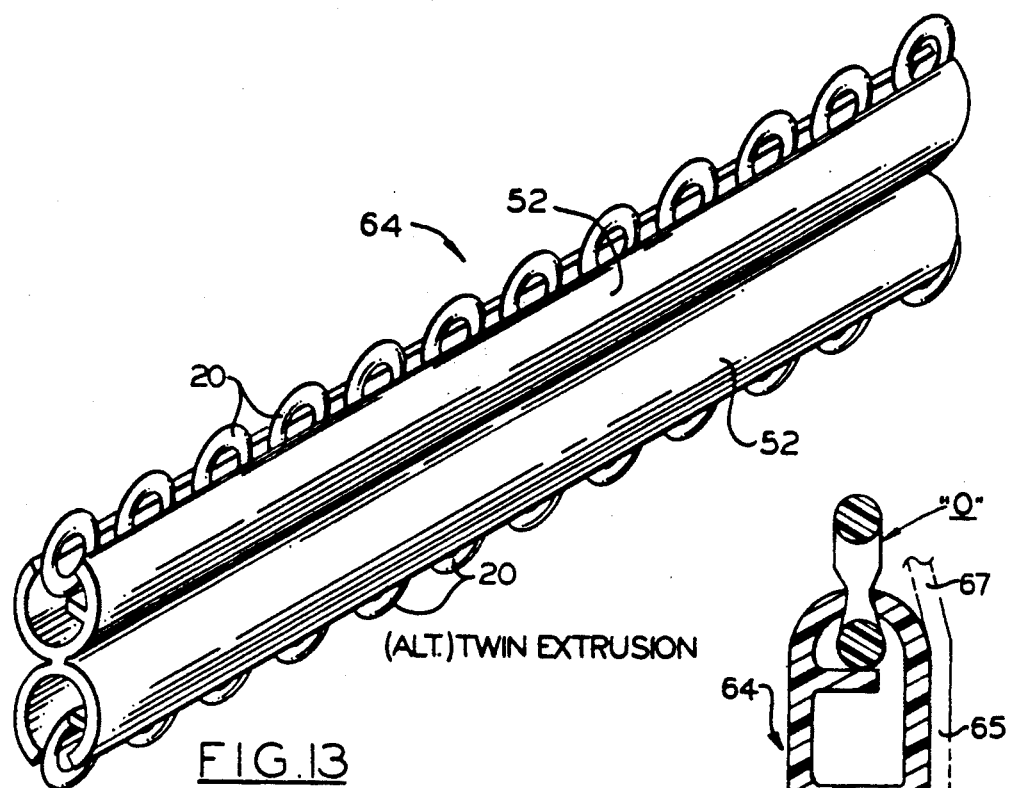
FIG.13 (ALT.) TWIN EXTRUSION
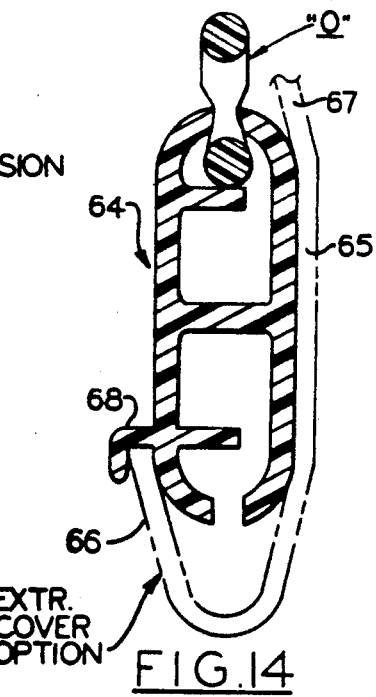
FIG.14 EXTR. COVER OPTION
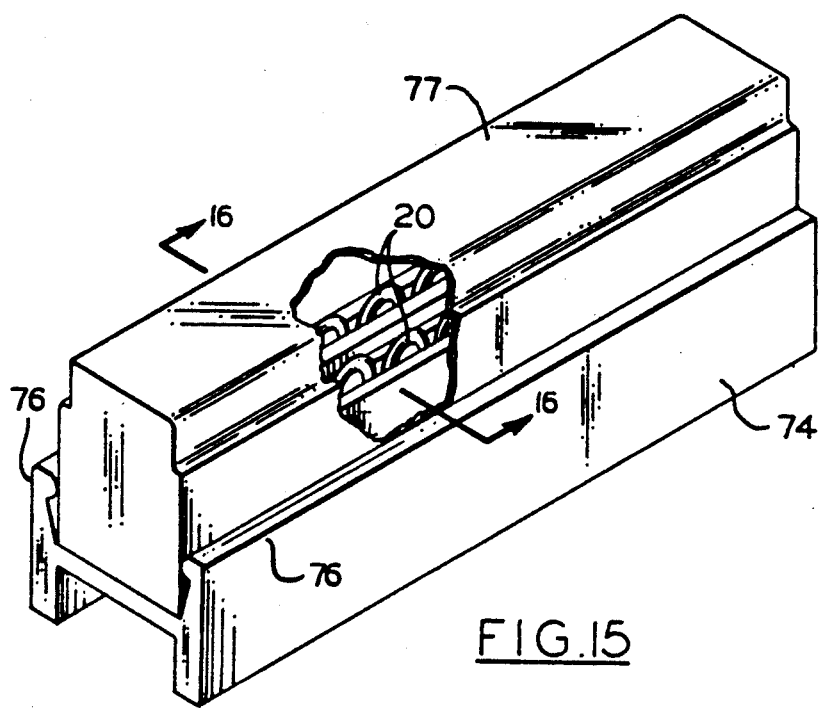
FIG.15

ASEPTIC ORTHODONTIC DISPENSING APPLIANCES

FIELD OF THE INVENTION

The present invention relates to devices for dispensing orthodontic appliances, and more particularly, for dispensing orthodontic O-rings.

BACKGROUND OF THE INVENTION

Orthodontic O-rings are used for securing orthodontic brackets to an orthodontic archwire. Because of their very small size, handling, storing and dispensing of orthodontic O-rings has been a problem. One suggested solution to this problem is illustrated by U.S. Pat. Nos. 4,217,686; 4,038,753. In these patents O-rings are provided on the runner on which they are molded. The O-rings are dispensed by pulling them off the runner. Since the supporting runner is made of the same material as the O-ring, the runner is quite flexible, therefore in order to be able to pull the O-rings off, a firm grip must be taken of the runner and O-rings, usually by use of the other hand. Additionally, if a tool of the type to be inserted in the O-ring opening is used to remove the O-rings, the back of the O-ring must be reinforced so as to prevent bending back of the O-ring. Thus it can be seen that the foregoing dispensing process significantly increases the risk of contamination of the O-rings to be dispensed. Additionally, this is usually accomplished by placing a finger against the backside of the O-ring. This dispensing process provides a torn section on the O-ring at the area where the O-ring was connected to the runner which may provide a weakened point for potential failure of the O-ring. This problem can be aggravated if the size of the connecting portion between the O-ring and runner is too large with respect to the size of the O-ring.

Applicants have invented an orthodontic dispensing device wherein the aseptic qualities of the appliances to be dispensed are maintained, the appliances are easily dispensed, the device is relatively low cost in manufacture and does not adversely affect the strength of appliances.

SUMMARY OF THE INVENTION

In one aspect of the present invention there is provided an orthodontic dispenser for dispensing elastomeric orthodontic O-rings. The dispenser includes a hand gripping portion and an elongated support section which is provided with means for either frictionally or clamping holding elastomeric orthodontic O-rings which can be easily dispensed.

In another aspect of the present invention there is provided a dispenser for dispensing elastomeric orthodontic O-rings wherein the O-rings are clamping held between engaging arms or in slot formed in the dispenser.

In yet another aspect of the present invention there is provided a dispenser for dispensing elastomeric orthodontic O-rings which includes a cylindrical housing for holding a plurality of orthdontic O-rings in stacked relationships. The cylindrical housing includes an opening at one end for allowing dispensing of the O-rings therethrough. Spring means are provided for biasing the O-rings against the end of the housing having the opening so as to maintain an O-ring in position for dispensing.

In another aspect of the present invention there is provided a dispenser for dispensing orthodontic O-rings which include at least one sealed package which comprise a pair of sheaths. A plurality of orthodontic O-rings are disposed therein.

DETAILED DESCRIPTION OF THE DRAWINGS

FIG. 9 is a side elevational view of the device illustrated in FIG. 8;

FIG. 10 is an enlarged cross-sectional view of FIG. 9 as taken along 10—10 with the O-rings removed;

FIG. 11 is a perspective view of yet another orthodontic dispensing device made in accordance with the present invention;

FIG. 12 is a perspective view of the device of FIG. 11 illustrating how the device may be initially filled with orthodontic appliances;

FIG. 13 is a perspective view of a modified embodiment of a dispensing device similar to that illustrated in FIG. 11;

FIG. 14 is a large cross-sectional view of another modified dispensing device made in accordance with the present invention having an optional cover;

FIG. 15 is a perspective view of a modified embodiment of an orthodontic dispensing device partially broken away made in accordance with the present invention;

Figure 19:
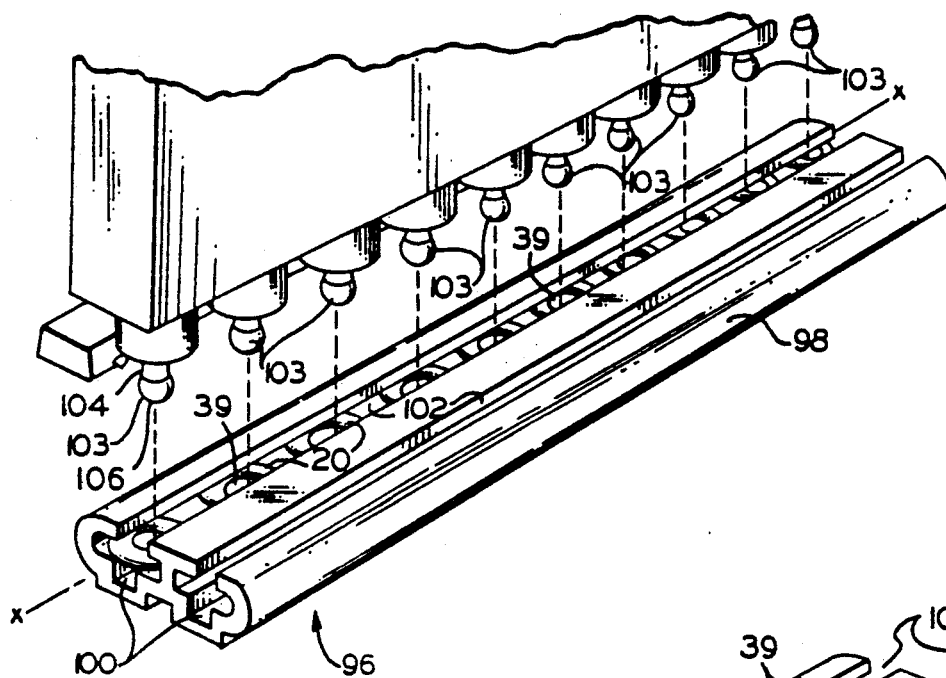
FIG. 19 illustrates an enlarged view of still another modified orthodontic dispensing device made in accordance with the present invention and how the device may be initially supplied with O-rings.
Figure 20:
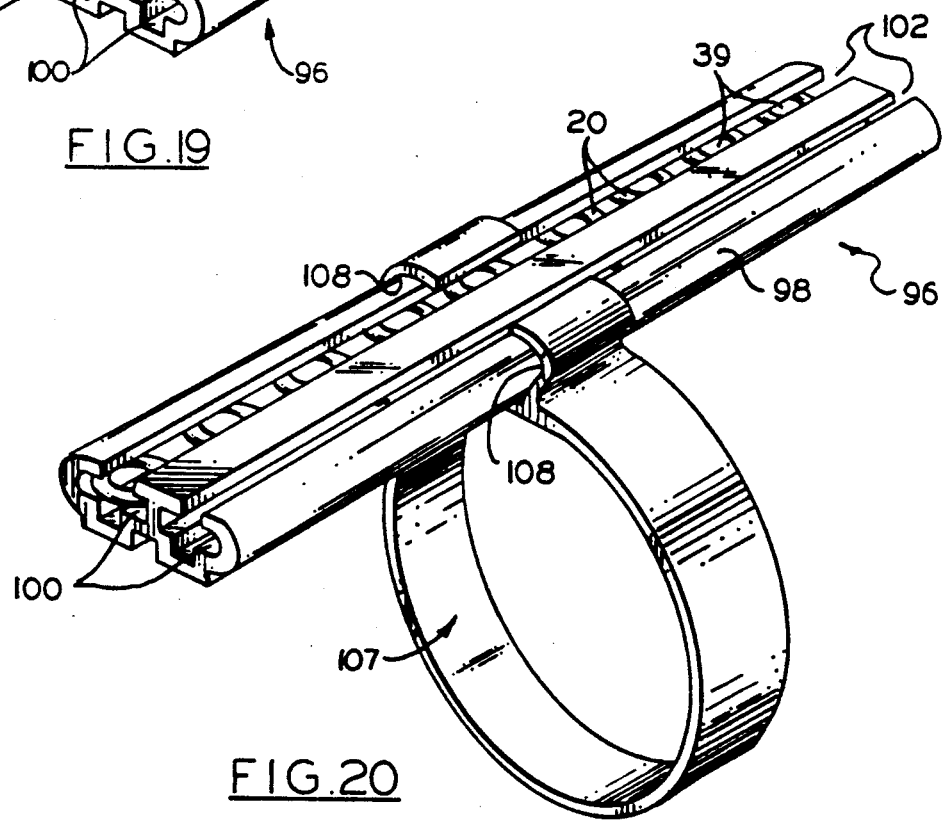
Figure 21:
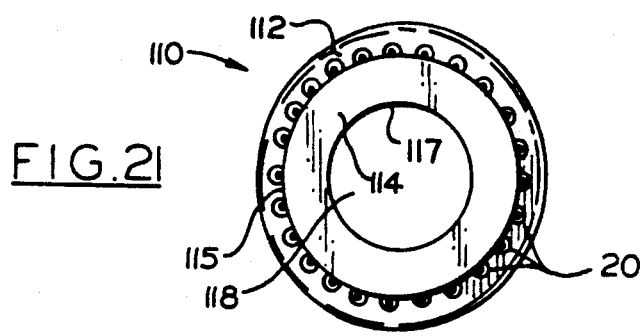
Figure 22:
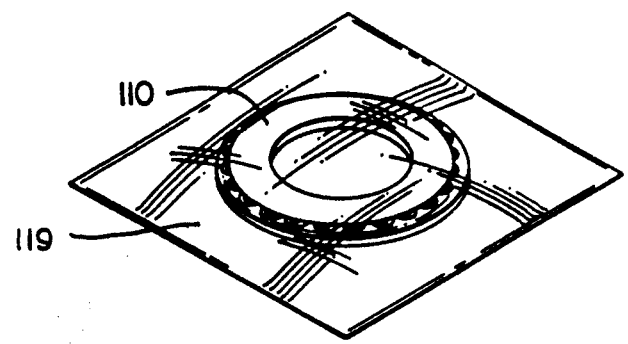
Figure 23:
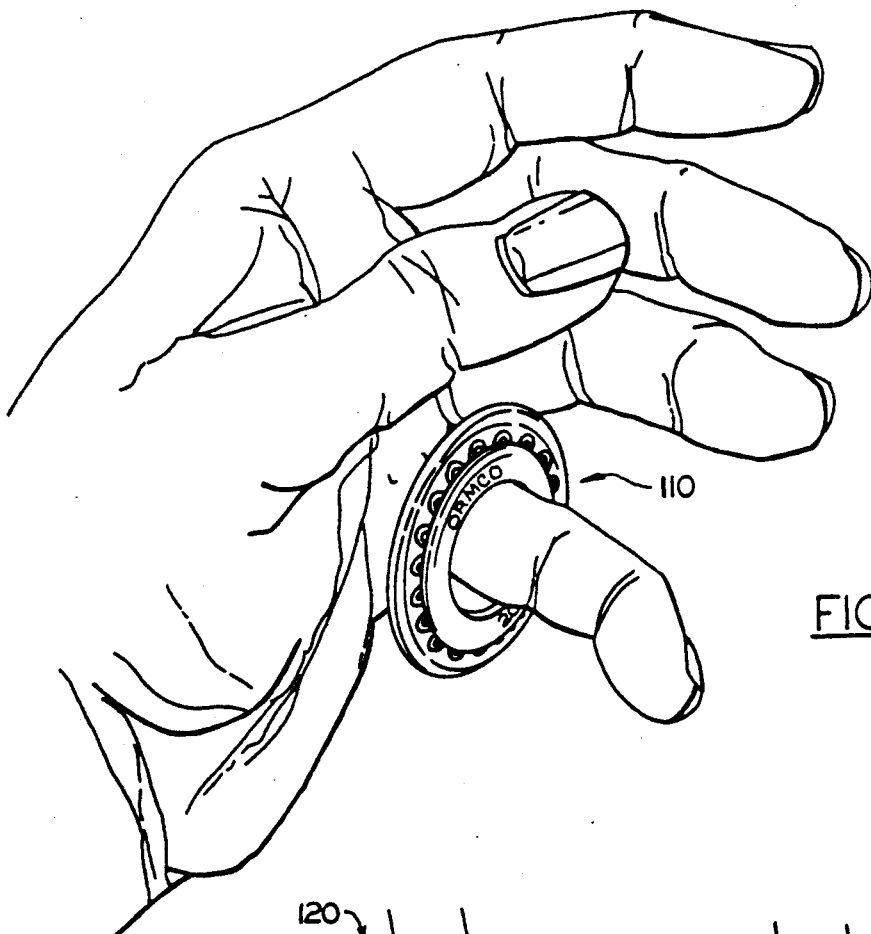
Figure 24:
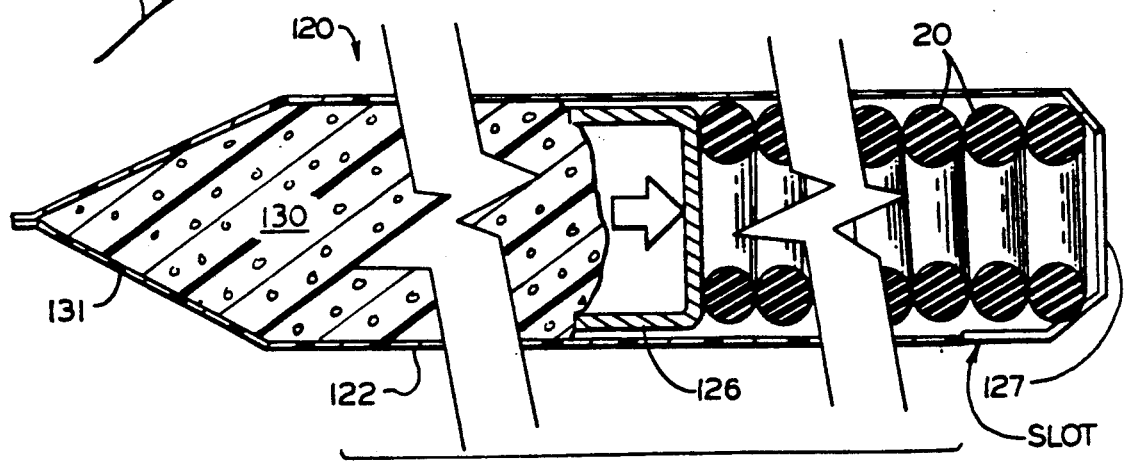
Figure 25:
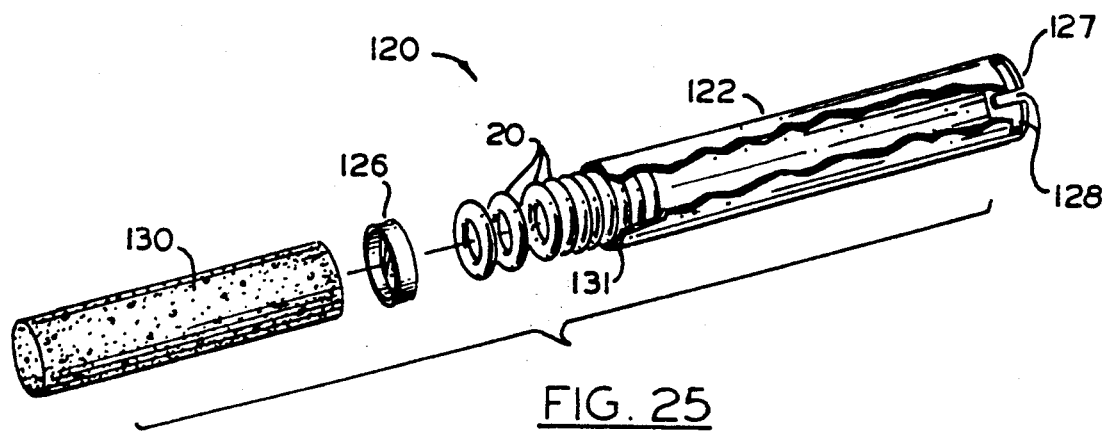
Figure 26:
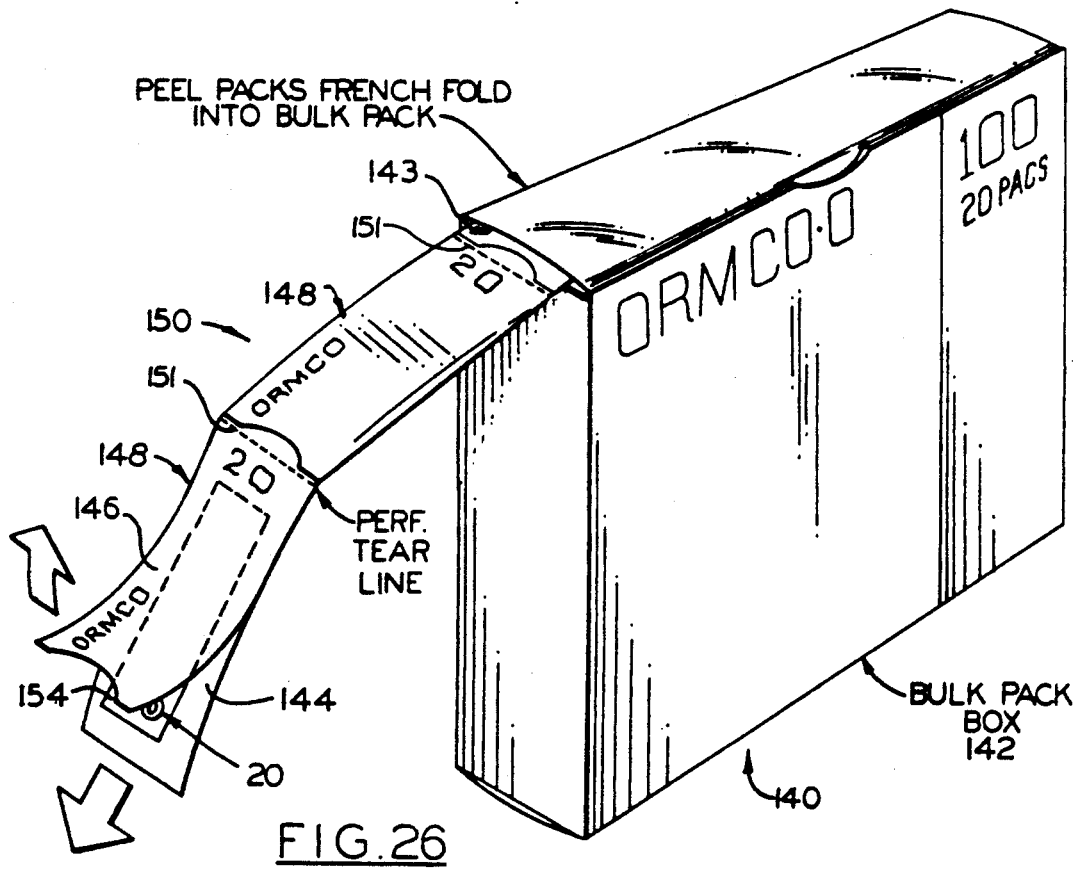
Figure 27:
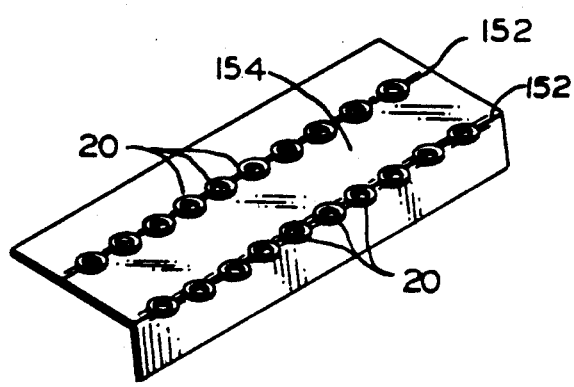

FIG. 20 a greatly enlarged view illustrating how the device of FIG. 19 as mounted within a ring holder;

FIG. 21 is a front elevational view of yet another embodiment of an orthodontic dispensing device made in accordance with the present invention;

FIG. 22 is a perspective view of the device of FIG. 20 as placed in a package;

FIG. 23 is a perspective view of the device of FIG. 21 as placed on the finger of the user;

FIG. 24 is a cross-sectional view of an alternate dispensing device made in accordance with the present invention;

FIG. 25 is an exploded partially broken away cross-sectional view of the device of FIG. 24 before O-rings are sealed therein;

FIG. 26 is a perspective view of yet another modified dispensing device made in accordance with the present invention prior to final assembly; and FIG. 27 is a perspective view of the dispensing board illustrated in FIG. 25 having O-ring mounted thereon.

DETAILED DESCRIPTION OF THE INVENTION

Figure 1:
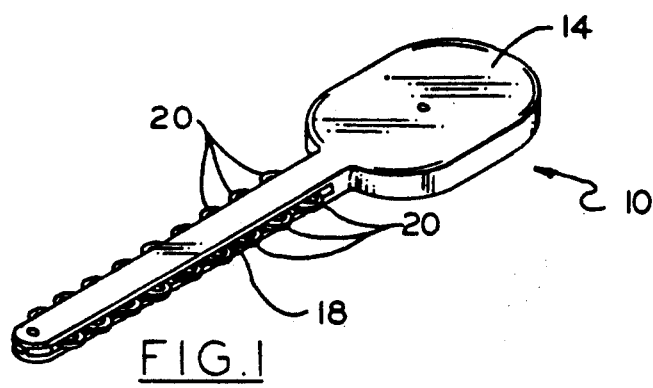
FIG. 1 illustrates a perspective view of an orthodontic dispensing device made in accordance with the present invention.
Figure 1A:
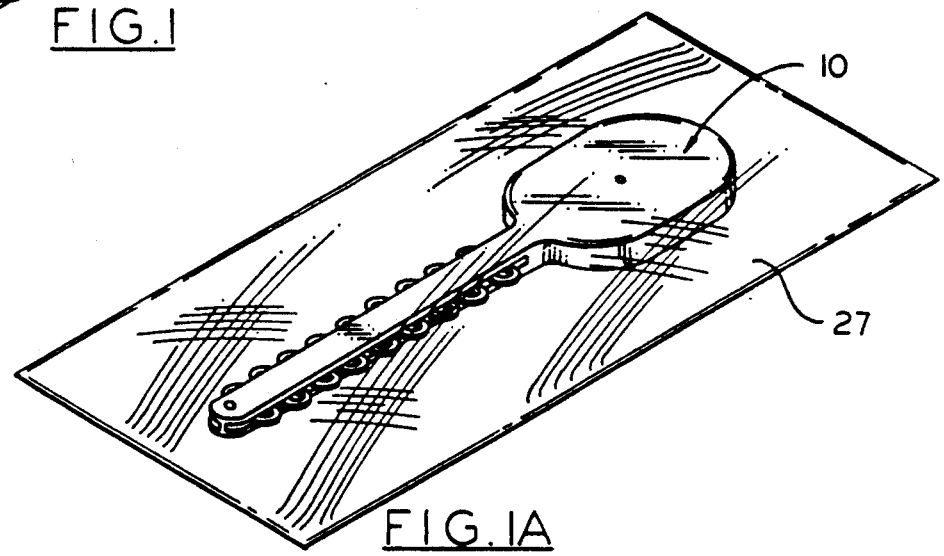
FIG. 1A is a view similar to FIG. 1 illustrating the orthodontic dispensing device placed on a package.
Figure 2:
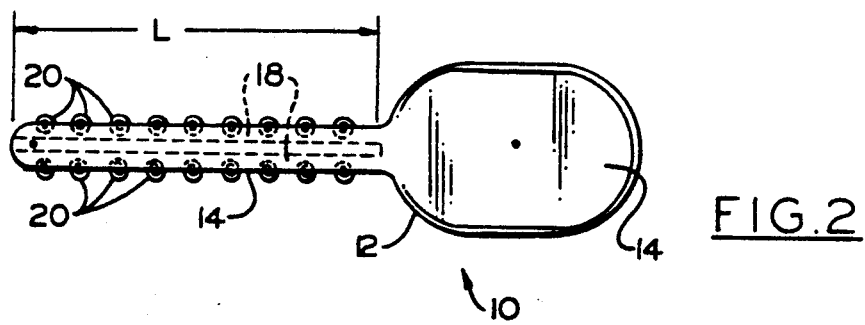
FIG. 2 is a top plan view of the device of FIG. 1.
Figure 3:
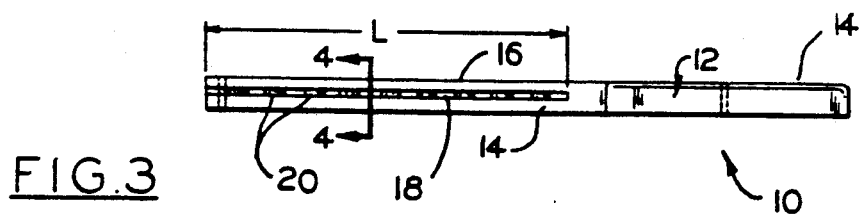
FIG. 3 is a side elevational view of the device of FIG. 1.
Figure 4:
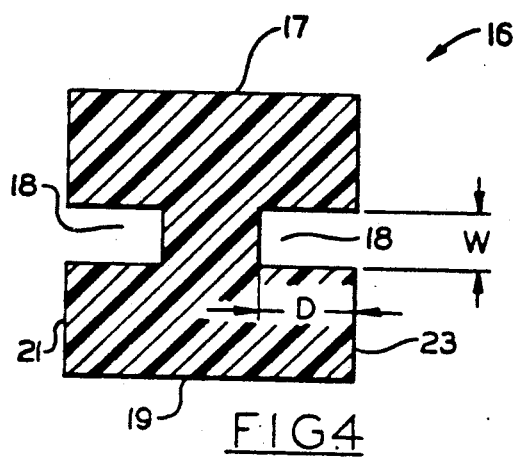
FIG. 4 is an enlarged cross-sectional view of the dispensing portion of the device of FIG. 3 as taken along line 4—4 with the O-rings removed from one slot.

Referring to FIGS. 1-4, there is illustrated a dispensing device 10 made in accordance with the present invention. In the particular embodiment illustrated, the dispensing device 10 comprises a rigid unitary support structure 12 having a finger gripping section 14 and an elongated dispensing section 16 which extends from one end of the finger gripping section 14 such that the fingers of the user do not come in close proximity to the dispensing section 16. Dispensing device 10 preferably is made of a rigid plastic material and in the particular embodiment illustrated, dispensing device 10 is made of polycarbonate. Dispensing section 16 has a generally rectangular cross-section shape as illustrated in FIG. 4, thus providing top, bottom, left and right sides 17, 19, 21, 23, respectively. However, the present invention is not so limited, as the cross sectional configuration of dispensing section 16 may take any desired form. The dispensing section 16 is provided with a pair of narrow grooves 18 disposed on the left and right sides 21, 23 of the dispensing section 16 as illustrated. The grooves 18 each have a width W and a depth D such that a plurality of orthodontic O-rings 20 may be placed in each groove 18 as illustrated. The width W is such that a small clamping force is applied against the sides of the O-rings 20 placed therein such that the O-rings 20 are firmly held in position yet can be easily pulled therefrom by use of a hand tool. Preferably, the dispensing device 10 is designed such that the dispensing section 16 has a length L such that a sufficient number of O-rings 20 are provided for use on a single patient. Preferably, the device 10 is provided with about 5 to 20 O-rings 20. In the particular embodiment illustrated, each groove 18 is provided with ten (10) orthodontic O-rings 20 in each groove 18. In order to dispense the O-rings 20, the user simply holds the gripping section 14 with his or her fingers and then takes a hemostat, or other similar type tool presently used in the prior art, to remove an O-ring 20 from the groove 18 in which it is placed. Thereafter, the O-ring 20 is placed on an orthodontic bracket as is customarily done in the prior art. The device 10 is preferably wrapped in its own separate package (see FIG. 1A) wherein device 10 is placed in a sealed plastic package 27. In this manner, the orthodontic O-rings 20 that are to be applied on a particular patient are not cross-contaminated with other dispensing devices and there is no danger of cross-contaminating with other stored O-rings as the particular device is desinged to be simply disposed of after a single use.

Figure 5:
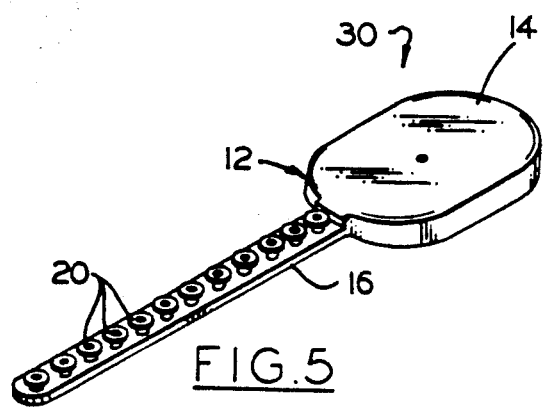
FIG. 5 is a perspective view of an alternate embodiment of a dispensing device made in accordance with the present invention.
Figure 6:
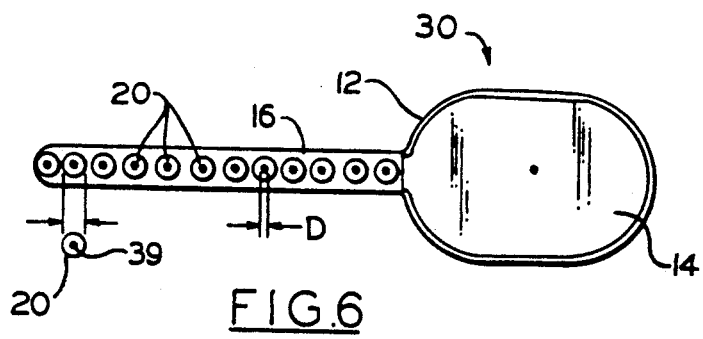
FIG. 6 is a front elevational view of the device illustrated in FIG. 5.
Figure 7:
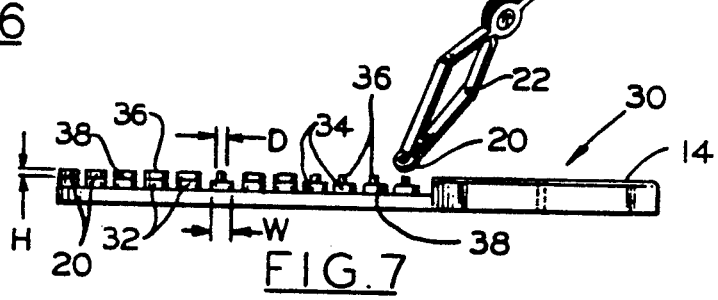
FIG. 7 is a side elevational view of the device illustrated in FIGS. 5 and 6 with some O-rings placed thereon.

Referring to FIGS. 5-7 there is illustrated a modified dispensing device 30 made in accordance with the present invention. In this particular embodiment the dispensing device 30 is similar to dispensing device 10 illustrated in FIGS. 1-4, like numerals indicating like parts. However, in this particular embodiment instead of having a pair of grooves 18, there is provided a plurality of spaced independent projections 32 extending from dispensing section 16. Projections 32, dispensing section 16, and finger gripping section 14, are preferably formed of a single unitary structure made of a plastic material. Each projection 32 comprises a base portion 34 adjacent dispensing section 16 and a narrow insert section 36 disposed at its upper end. Insert section 36 has a cross-sectional diameter D less than that of the cross-sectional width W of base portion 34 such that a support shelf 38 is formed at their juncture. The diameter D of insert section 36 is designed to frictionally engage the opening 39 of O-ring 20 and hold the single O-ring 20 firmly thereon. The insert section 36 has a height H sufficient to engage the opening 39 of O-ring 20. In order to dispense the O-rings 20, a hemostat 22 (as illustrated in FIG. 7) or other similar instrument is used to grip the outer periphery of O-rings 20 and pull O-ring 20 off insert section 36. As can be seen, the fingers of the user do not come in close proximity to the O-rings being dispensed, thereby, minimizing any potential contamination. Dispensing device 30 is similar to dispensing device 10 in that they are both designed to be disposable after a single patient use. Accordingly, the dispensing device 30 is designed to have about twelve (12) to twenty (20) O-rings, and in the particular embodiment illustrated, 10 projections 32 are provided for holding individual O-rings. In the particular embodiment illustrated projections 32 are shown to be only on one side of elongated dispensing section 16, however, projections 18 may be provided on more than one side if so desired.

Figure 8:
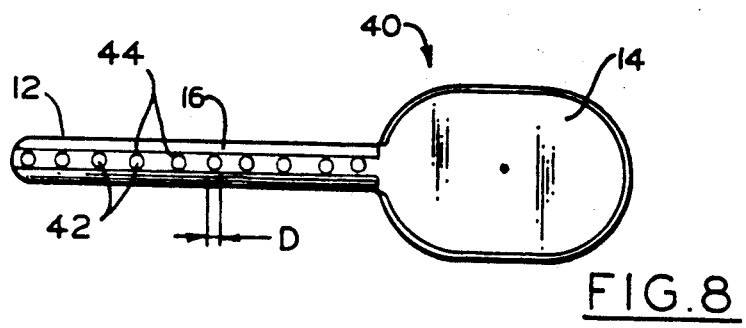
FIG. 8 is a front elevational view of another modified dispensing device made in accordance with the present invention.

Referring to FIGS. 8-10 there is illustrated a dispensing device 40 similar to dispensing device 30. Dispensing device 40 is provided with a plurality spaced projections 42 each having a generally circular cross-sectional figuration of diameter D. The projections 42 are designed to fit within the opening 39 of O-rings 20 in the same manner as insert section 36 of dispensing device 30. In this embodiment the dispensing section 16 has a cross-sectional configuration which makes it easier to dispense the orthodontic O-rings 20. As illustrated in FIG. 10, the dispensing section 16 is provided with a generally honeycomb cross-sectional configuration having a top side 41, a bottom side 43 and four angled sides 45. In the particular embodiment illustrated, the four sides 45 each have substantially equal length and the top and bottom sides 41, 43, each have a length L2 equal to or slightly larger than the diameter D of insert 44 so that a hemostat, or other tool which is used to remove the O-ring, can be easily positioned on both sides of the orthodontic O-ring thus making it simpler and easier to remove the O-ring therefrom. Sides 45 are oriented at an angle α with respect to a line parallel to side 41, 43. Angle α is preferably greater than 45°. The O-rings 20 of dispensing device 40 are simply removed by pulling each O-ring off projection 42. The length and angular orientation of sides 45 are selected to faciliate removal of the O-ring. In the particular embodiment illustrated sides 45 have a length L2 of approximately 0.042 inch and sides 45 are disposed at an angle of about 60°. However, it is to be understood the cross-sectional shape of elongated section 16 may be varied as desired. So as to allow easy removal of O-rings 20. For example, but not by way of limitation, sides 45 may be substantially perpendicular to sides 41, 43 so as to form a generally rectangular shape having a width only slightly larger than insert section 44.

Referring to FIGS. 11 and 12 there is illustrated yet another dispenser 50 made in accordance with the present invention. The dispensing device 50 comprises an elongated rigid tubular member 52 which is preferably extruded. Tubular membrane 52 may be made of any suitable material which may be extruded. In the particular embodiment illustrated, tubular membrane 52 is made of a plastic. Tubular member 52 includes a pair of flexible arms 54 which are spaced apart so as to form a small axially extending slot 56 along member 52. The arms 54 are made flexible by the appropriate selection of the thickness of the arms, their configuration and the material from which they are made. The slot 56 having a width S of sufficient size so that when an orthodontic O-ring 20 is placed within slot 56, the O-rings 20 will be firmly held in position between arms 54. An internal shelf 57 is preferably provided internally of tubular member 52, for limiting the amount of the orthodontic O-rings 20 may be place into tubular member 52, thus allowing a sufficient amount of O-ring to be exposed so it can be easily grasped and dispensed. The amount of clamping force provided by arms 54 is of sufficient amount so as to firmly grasp and hold the O-rings 20 yet small enough to allow easy removal by pulling the O-rings 20 by a hemostat or other similar type tool used to ligate orthodontic O-rings.

FIG. 12 illustrates how the O-rings may be initially inserted in dispenser 50. A plurality of O-rings 20 that have been molded on to a runner 58 are placed in the same longitudinal plane as slot 56. An anvil 59 is caused to move axially along tube 52 as indicated by the arrow 60 to spread flexible arms 54 so as to open slot 56 behind the anvil 59. The anvil is of sufficient size and shape so that the slot is opened a sufficient amount to allow the easy insertion of O-rings 20. The O-rings 20 are inserted into slot 56 immediately behind anvil 59. As anvil 59 moves along slot 56, slot 56 closes so as to clamp the O-rings that have been inserted therein. The rate of speed at which the O-rings are placed within the tubular member 52 relates to the speed at which the anvil 59 proceeds along the length. Once the O-rings 20 have been clamped between the arms 54 a knife or other sharp instrument comes along and cuts the connecting part 61 connecting the O-ring 20 to runner 58. Since O-rings 20 are cut from the runner 58 there is no torn or rough section where the O-ring has been removed from the runner 58. The procedure for installing the O-rings into member 59 can be easily automated. Thereafter, tubular member 52 may be cut into the appropriate length to provide the appropriate member O-ring for dispensing. Preferably the length of the tubular member 52 is selected so as to provide a sufficient number of O-rings for single use. The tubular member 52 and O-rings 20 are then individually placed in a package similar to that previously discussed with the other dispensing devices.

It is to be understood that various other cross-sectional configurations may be used for tubular member 52 as desired. For example, in FIG. 13 a modified dispensing device 64 is illustrated. Dispensing device 64 is similar to dipensing device 50 except two separate tubular members 52 are provided which are co-extruded as a single unit.

Referring to FIG. 14 there is illustrated a cross-sectional view and another modified dispensing device 64 which can also be extruded. Dispensing device 64 is similar to dispensing device illustrated in FIG. 13 except that dispensing device 64 has slightly different cross-sectional configuration and an optional cover 65 is provided such that the O-rings 20, located in the bottom half, are protected and will not come in contact with the hand of the user as the remaining O-rings on the opposite side are dispensed. Cover 65 has a generally C-shaped cross-sectional configuration. One end 66 of cover 65 locks in a curved hook 68 integrally formed on device 64. The other end 67 is bent so that cover 66 snaps on device 64. It is to be understood that any other means may be provided to secure cover 65 to device 64.

Figure 16:
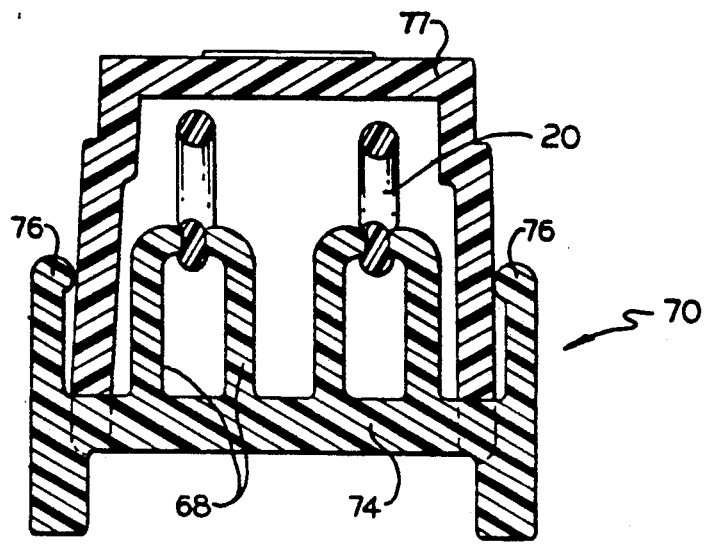
FIG. 16 is an enlarged cross-sectional view of the device of FIG. 15 taken along line 16—16.

Referring to FIGS. 15 and 16 there is illustrated another form of the present invention wherein an extruded or molded tubular member 70 is provided having two pairs of flexible arms which clamp and engage O-rings 20. The flexible arms 68 are provided and are integrally formed with a base portion 74. Base portion 74 is further provided with a pair of outer flexible arms 76 which are used to retain a cover 77 so as to protect the orthodontic O-rings placed between arms 68. The cover 77 is simply held in place by the clamping force exerted by arms 76.

Figure 17:
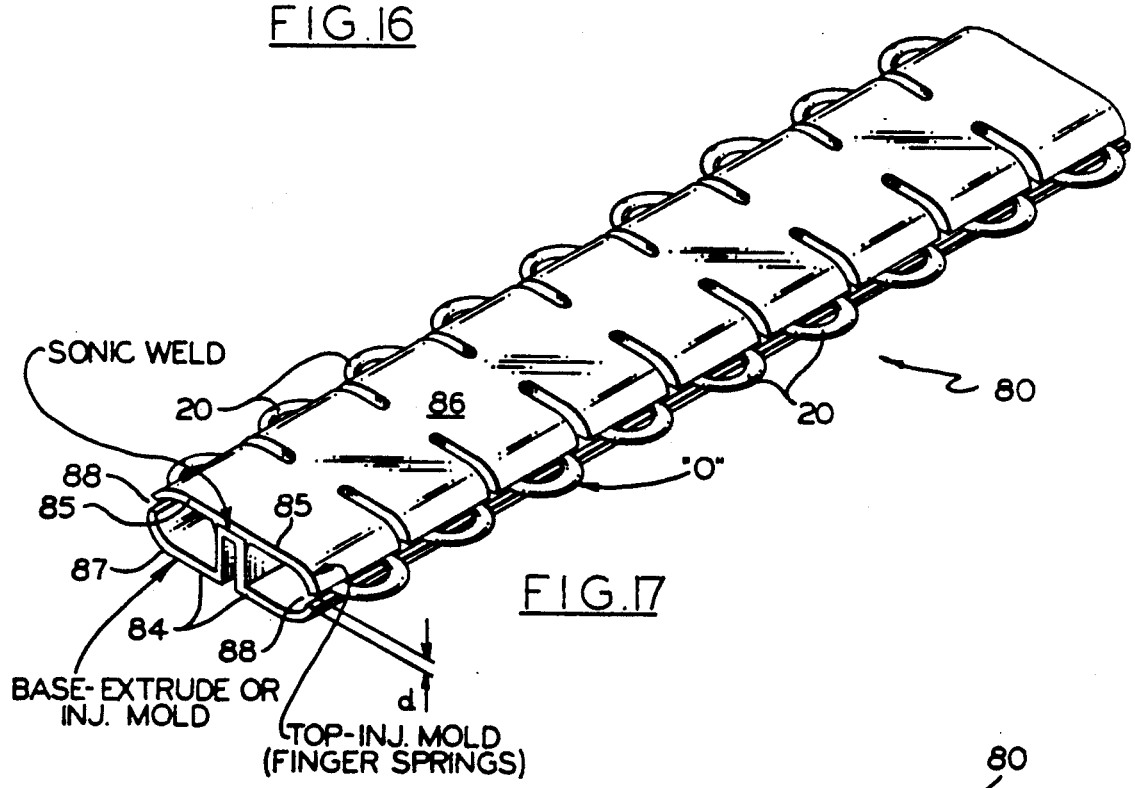
FIG. 17 illustrates a perspective view of still yet another modified orthodontic dispensing device made in accordance with the present invention.
Figure 18:
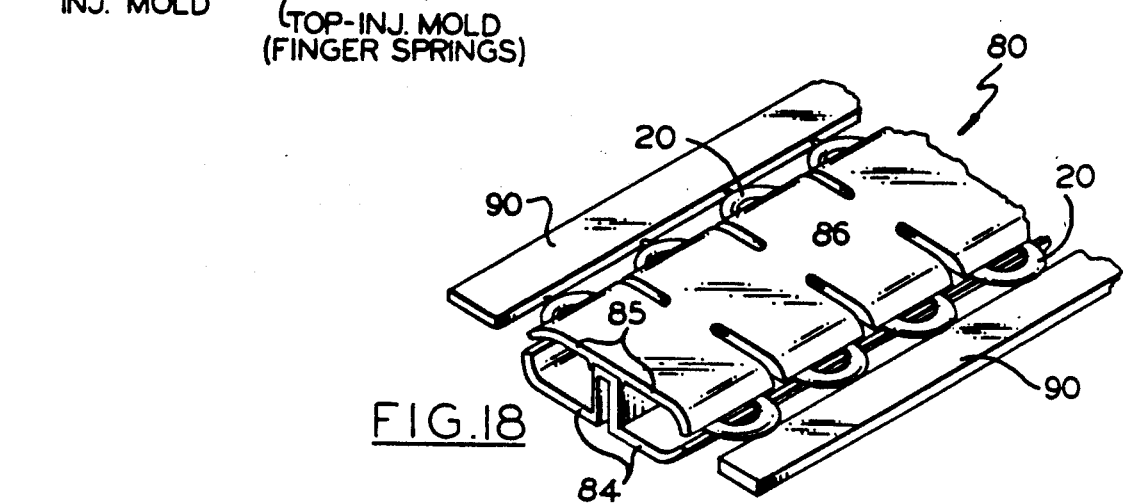
FIG. 18 illustrates the device of FIG. 17 and how it is initially supplied with orthodontic O-rings.

Referring to FIGS. 17 and 18 there is illustrated another dispensing device 80 made in accordance with the present invention. In this particular embodiment, dispensing device 80 is composed of two separate molded plastic pieces which snap together to provide two pairs of flexible clamping arms 84, 85 for holding O-rings 20 therebetween. Device 80 comprises an upper half 86 and the bottom half 87 which are secured together at a common center region. The upper and bottom halves 86, 87, each provide one half of the two pairs of arms 84, 85. When assembled each pair of arms 84, 85 provide a slot 88 therebetween having a spacing of sufficient width so as to clamp and firmly hold the O-rings 20 therebetween. An advantage of this particular embodiment is that the O-rings may be initially installed in device 80 without the aid of any anvil or other type to open slot between arms 84. In this particular embodiment a runner 90 having a plurality of O-rings 20 molded thereon, as illustrated, in FIG. 18 are provided adjacent arms 84 before assembly. The runner 90 and O-rings 20 are positioned with respect to the bottom half 87 and thereafter the top half 86 is secured to the bottom half 87 to clampingly hold the O-rings 20 therebetween. Thereafter the O-rings are severed from its respective runner 90 by any appropriate cutting means. In the present invention the O-rings are severed from runner 90 by a sharp knife so as to provide a smooth shape on the outer periphery of the O-ring 20. In the particular embodiment illustrated the bottom half 87 and upper half 86 are secured together by ultrasonic welding, however the present invention is not limited to such. For example, if desired, the upper and bottom halves 86, 87 may be secured together by an adhesive or any other means so desired. The O-rings 20 are removed from device 80 much in the same way as the other devices in that a hemostat or other similar type tool is used to grab the exposed portion of the O-ring and remove it from the clamping arms 84. Device 80, as in the dispensing devices previously described, is preferably designed for single patient use.

Referring to FIGS. 19 and 20 there is illustrated yet another modified dispensing device 96 made in accordance with the present invention. In this embodiment there is provided an extruded body 98 made of any suitable material having a pair of axially extending channels or recess 100 formed therein. The channels 100 each have a cross-sectional configuration which corresponds to the side cross-sectional configuration of an O-ring 20 as illustrated. The body 98 is provided with a longitudinal extending slot 102 which aligns with the center opening 39 of the O-rings 20. The slot 102 provides a means to allow insertion and/or removal of a tool for removing or installing O-rings 20. In one method of installing O-rings 20, the O-rings are placed on a plurality of insertion pins 103 as illustrated in FIG. 19. The insertion pins 103 are shaped so that O-rings can be easily placed thereon and later removed. In the particular embodiment illustrated, each pin 103 comprises a cylindrical neck portion 104 which terminates in a bulb head 106. The head 106 is sized so as to firmly hold or engage opening 39 of O-ring 20, but also allow O-ring to be pulled off after sufficient amount of force is applied. The O-rings 20 are mounted within the channel by axially moving the pins 103 along axis x-x such that the O-rings 20 slide within the channels 100. After positioning O-rings properly within the channel the pins 103 are lifted up leaving the O-rings 20 in channels 100. The channels 100 each have a shape configuration such that the O-rings 20 can easily slide therein for removal, but provides a sufficient clamping force to hold O-rings 20 firmly in place when no force is being applied. In the embodiment illustrated, two channels 100 are provided, however, the present invention may have a single, or as many channels as desired.

Referring to FIG. 20, there is illustrated an optional finger holder 107 which is provided with a channel recess 108 which is capable of receiving the body 98 of device 96. In this way the device 80 may be placed on one hand and a tool placed in the other hand of the user can be used to remove the O-rings therefrom in a quick and efficient manner.

Referring to FIGS. 21, 22 and 23 there is illustrated another dispensing device 110 made in accordance with the present invention. The device 110 comprises a first wall 112 and a second wall 114 spaced from the first wall 112 so as to provide an annular groove 115 therebetween. In the particular embodiment illustrated the walls 112, 114 of device 110 are molded as a single unitary structure of an flexible material wherein an annular inner portion 117 connects walls 112, 114. An opening 118 is provided therein for the placement of a finger. A plurality of O-rings are placed in the annular groove 115 formed between the first and second walls 112, 114. This structure is particularily suited for tools which are placed directly in the opening of the O-rings as the wall 112 provides support to the O-rings. The device 110 as in the other devices is preferably provided with a sufficient number of O-rings for single patient use. As illustrated in FIG. 23 the device 110 is provided in a sealed plastic cellophane package 119 to minimize contamination of the O-rings thereof.

Referring to FIG. 24 there is illustrated another device 120 made in accordance with the present invention. Device 120 comprises a plastic housing 122 which takes the form of an elongated, hollow, cylindrical, shell which can hold a plurality of O-rings 20 in stacked relationship as illustrated in FIG. 24. The device 120 further includes spring means to bias a piston 126 against the bottom of the plurality of stacked O-rings 20 such that the O-rings 20 are pushed against one end 127 of housing 122. An opening 128 is provided at end 127 and has a configuration so as to allow the O-rings 20 to be dispensed therefrom through the use of a hemostat or other similar tool. In the particular embodiment illustrated, opening 128 is designed to allow a tool of the type that fits within the center opening to be placed through the top and the O-ring slide out the side. The spring means in the particular embodiment illustrated comprises an open cell foam 130 which pushes on a piston 126. As each O-ring is removed the piston is caused to move in toward end 127 forcing the next adjacent O-ring 120 against the top of housing 122. In the particular embodiment illustrated the piston 126 provides a constant even force to the bottom of the lower most O-ring 20. However, piston 20 may be omitted as desired such that the spring means exerts a force directly on the lower most O-ring 20. In the embodiment illustrated the bottom 131 of housing 122 is heat sealed after loading of the O-ring piston and spring means therein. In the particular embodiment illustrated the housing 122 is made of a plastic material. Initially housing 122 has a generally cylindrical configuration as illustrated FIG. 25. After the O-rings are inserted the piston 126 is next inserted and then spring means is disposed therein. Thereafter, the bottom 131 is pinched off and heat sealed to retain the contents therein.

Referring to FIGS. 26-27, there is illustrated another dispensing device 140 made in accordance with the present invention. In this embodiment there is provided a package 142 in the shape of a box having disposed therein an elongated strip assembly 150 which comprises a plurality of packets, each having an inner sheath 144 and an outer sheath 146 secured to each other at their periphery. The strip assembly is dispensed throughout slot 143 in package 142. The strip assembly is provided with a plurality of spaced tear lines 151 which provide means for separating individual packets 148. Preferably, the entire outer periphery of each packet 148 is sealed so as to provide a hermetically sealed package. Each packet 148 includes a plurality of orthodontic O-rings 20 disposed between sheaths 144, 146. The outer sheath 146 is capable of being easily removed off outer sheath 146 by peeling it off as illustrated in FIG. 26 to allow access and dispensing of O-rings 20 disposed therebetween. A sufficient number of O-rings are provided for a single patient use. Therefore, the user may take as many packets 148 as needed for the particular procedure being done. In the preferred embodiment the orthodontic O-rings 20 are placed on a dispensing board 154 placed between sheaths 144, 146. In the embodiment illustrated the O-rings 20 are adhered to board 154 by the use of a tacky adhesive. The O-rings 20 are preferably disposed on board 157 in parallel rows. The board 154 in the preferred embodiment illustrated is provided with a pair of crease lines 152. The O-rings 20 are disposed on the board 154 so that each row coincides with its respective crease line 152. In order to dispense the orthodontic O-rings a hemostat or other similar type tool is used to clamp on to one edge of the O-ring 20. To assist in removing the O-ring from board 154, the board may be bent back as illustrated in FIG. 27 along crease line 152 so as to allow a hemostat or other tool to easily clamp both sides of the O-ring 20. In the preferred form of the present invention the crease lines 152 are provided parallel to the longitudinal axis of each row. However, the present is not limited to such. Crease line 152 may be providing in any desired orientation such that a portion of the O-ring is presented for easy removal thereof. As previously mentioned the O-rings 20 are held on to the board 154 by an appropriate tacky adhesive. Adhesive is such that the O-rings 20 are simply held in position yet allows each removal of the O-ring 20 therefrom. An example of appropriate adhesive that may be used is a double stick adhesive tape sold by 3M under the Scotch trademark. However, any other adhesive or tape may be used as desired. In the embodiment illustrated the packets 48 are formed in an elongated strip, however, the present invention is not so limited. The packets may also be individually placed in a container for individual dispensing.

It is to be understood that variouss changes may be made to the present invention without departing from the scope of the present invention; the following claims defining the scope of the present invention. For example, various other material not described may be used for the dispensing devices of the present invention. Additional various other configurations and shapes in the dispenser may be provided other than has been illustrated. Further, the dispenser may be modified to hold any size O-rings or hold other equivalent type orthodontic appliance such as spacers.

What is claimed is:

1. An orthodontic O-ring dispensing device comprising:
   at least one elongated hollow tube structure having an elongated slot which extends along the longitudinal axis of said tube to at least one end of said tube, said slot forming a pair of engaging flexible arms for clamping holding a plurality of orthodontic O-ring; and
   a plurality of O-rings disposed in said slot, each O-ring being clamped in position between said engaging arms of said tube.

2. A dispenser according to claim 1 wherein said tube has an internal shelf for limiting the amount the O-rings may be inserted in said tube.

3. A dispenser according to claim 1 wherein a pair of tube structures are provided for holding a plurality of O-rings.

4. A dispenser according to claim 3 wherein a cover is provided for protecting said O-rings in one of said slots.

5. A method of filling a dispenser for dispensing a plurality of orthodontic O-rings wherein said dispenser comprise an elongated hollow tube structure having an elongated slot which extends along the longitudinal axis of said tube to at least one end of said tube, said slot forming a pair of engaging flexible arms for clamping holding a plurality of orthodontic O-rings, comprising the steps of:
   placing a separating anvil in said slot,
   moving said anvil along said slot so as to separate said arms to form a wider access;
   placing an orthodontic O-ring in the said widened area;
   clamping holding said anvil and allowing said arms to return to their normal position.

6. An orthodontic O-ring dispenser comprising:
   a body portion having at least one elongated internal channel which extends to at least one end of said body portion, said channel capable of frictionally engaging a plurality of O-rings one behind the other therein; and
   a plurality of O-rings are disposed within said channel, said O-ring being dispensed by moving said O-ring out the end of said channel.

7. A dispenser according to claim 6 wherein two elongated channels are provided.

8. A dispenser according to claim 6 further comprising a longitudinal slot associated with each of said channels and positioned so as to align with the centers of said O-rings so as to allow access to the center opening in said O-rings.

9. A method of filling a dispenser for dispensing orthodontic O-rings comprising a body portion having at least one elongated internal channel which extends to at least one end of said body for holding a plurality of orthodontic O-rings, said body having a slot associated with at least one elongated said channel and aligned with the center of said O-rings so as to allow access to the center opening in said O-rings, comprising the steps of:
   moving a plurality of O-ring in an axial direction in said channel by using a mounting pin which fits within the center of said O-ring;
   leaving in position said O-rings in said channel by pulling said pin out of said opening.

* * * * *